United States Patent
Schwarzberg et al.

(10) Patent No.: US 8,560,336 B2
(45) Date of Patent: *Oct. 15, 2013

(54) SYSTEM AND METHOD FOR INCREASING COMPLIANCE WITH A HEALTH PLAN

(75) Inventors: Robert Schwarzberg, Boca Raton, FL (US); Marion Zabinski, San Diego, CA (US); Rene Melton, Delray Beach, FL (US); Timothy J. Dion, Parkland, FL (US)

(73) Assignee: Humana Innovations Enterprises, Inc., Louisville, KY (US)

(*) Notice: Subject to any disclaimer, the term of this patent is extended or adjusted under 35 U.S.C. 154(b) by 1096 days.

This patent is subject to a terminal disclaimer.

(21) Appl. No.: 12/118,939

(22) Filed: May 12, 2008

(65) Prior Publication Data

US 2009/0076335 A1 Mar. 19, 2009

Related U.S. Application Data

(63) Continuation-in-part of application No. 12/117,190, filed on May 8, 2008, now Pat. No. 8,463,618, and a continuation-in-part of application No. 11/856,917, filed on Sep. 18, 2007.

(51) Int. Cl.
- G06Q 10/00 (2012.01)
- G06F 7/00 (2006.01)
- A63B 71/00 (2006.01)

(52) U.S. Cl.
USPC .......... 705/2; 705/3; 707/104; 482/8

(58) Field of Classification Search
USPC ................................................. 705/2
See application file for complete search history.

(56) References Cited

U.S. PATENT DOCUMENTS

| 5,377,258 A | 12/1994 | Bro |
| 5,673,691 A | 10/1997 | Abrams et al. |

(Continued)

FOREIGN PATENT DOCUMENTS

| WO | 9944494 | 9/1999 |
| WO | 2006021956 | 3/2006 |
| WO | 2006138680 | 12/2006 |

OTHER PUBLICATIONS

Be Well Mobile, A Picture of Health, Patient Engagement Software That Works, http://www.bewellmobile.com; http://www.bewellmobile.com/products-services.html; http://www.bewellmobile.com/biographies.html; http://www. bewellmobile.com/patient-engagement.html, 6 pages from website, Copyright 2006, Feb. 21, 2007.

(Continued)

*Primary Examiner* — Hiep V Nguyen
(74) *Attorney, Agent, or Firm* — Standley Law Group LLP

(57) ABSTRACT

System and method to determine user compliance with personalized diet and exercise plans by analyzing responses to messages about the plans. An expert system has a number of stored messages and display characteristics from which it chooses. The expert system generates message relating to the user's diet or physical activity that are sent to a user's mobile device and analyzes responses. Display characteristics change periodically and compliance data relating to the user's adherence to the plan when certain display characteristics are used is stored (e.g., meal plan adherence, acceptance of specific food selections, and adherence to instructions and advice in messages). The expert system then determines which messages and display characteristics achieve the greatest compliance to the dietary and physical activity schedule and goals.

15 Claims, 3 Drawing Sheets

(56) References Cited

U.S. PATENT DOCUMENTS

| | | |
|---|---|---|
| 5,832,448 A | 11/1998 | Brown |
| 5,890,128 A | 3/1999 | Diaz et al. |
| 5,897,493 A | 4/1999 | Brown |
| 5,954,510 A | 9/1999 | Merrill et al. |
| 6,039,688 A | 3/2000 | Douglas et al. |
| 6,246,992 B1 | 6/2001 | Brown |
| 6,366,871 B1 | 4/2002 | Geva |
| 6,602,191 B2 | 8/2003 | Quy |
| 6,811,516 B1 | 11/2004 | Dugan |
| 6,936,007 B2 | 8/2005 | Quy |
| 6,968,375 B1 | 11/2005 | Brown |
| 6,976,958 B2 | 12/2005 | Quy |
| 7,090,638 B2 | 8/2006 | Vidgen |
| 7,156,809 B2 | 1/2007 | Quy |
| 7,222,054 B2 | 5/2007 | Geva |
| 2002/0128804 A1 | 9/2002 | Geva |
| 2003/0152607 A1* | 8/2003 | Mault .................. 424/439 |
| 2005/0021361 A1 | 1/2005 | Huang et al. |
| 2005/0021372 A1 | 1/2005 | Mikkelsen et al. |
| 2005/0101845 A1* | 5/2005 | Nihtila ................. 600/300 |
| 2005/0113649 A1 | 5/2005 | Bergantino |
| 2005/0113650 A1 | 5/2005 | Pacione et al. |
| 2006/0041452 A1 | 2/2006 | Kulkarni |
| 2006/0058586 A1 | 3/2006 | Humble |
| 2006/0064447 A1 | 3/2006 | Malkov |
| 2006/0178907 A1 | 8/2006 | Humble |
| 2006/0189853 A1 | 8/2006 | Brown |
| 2006/0199155 A1 | 9/2006 | Mosher |
| 2006/0205564 A1* | 9/2006 | Peterson .................. 482/8 |
| 2006/0287883 A1 | 12/2006 | Turgiss et al. |
| 2007/0021984 A1 | 1/2007 | Brown |
| 2007/0030339 A1 | 2/2007 | Findlay et al. |

OTHER PUBLICATIONS

BeWell Mobile Forms Partnership with Wipro for Disease Management, BeWell Also Named Finalist in Global Software Competition Conduct by Qualcomm, Press Release, Dec. 6, 2006.

Diet Tiny Assist, http://www.wimos.com/diet.html, 4 pages from website, Feb. 16, 2007.

Welcome to Health Hero Network, Making Connections for Life, Heath Buddy System, http://www.healthhero.com/products services/products services.html; http://www.healthhero.com/products services/peripherals.html, 4 pages from website, Copyright 2006, Feb. 12, 2007.

Palm OS, Keyoe, Software products to organize and enhance your life, http://www.keyoe.com/DEA Handheld.htm, 8 pages from website, Copyright 2000-2007, Last modified: Dec. 2, 2006, Feb. 16, 2007.

Card Guard AG and Humana form new company to provide innovative wireless platform for wellness and disease management, Press Release, Oct. 17, 2005.

Ali, Sarmad, Technology Enlisting cellphones to fight cellulite, The Wall Street Journal, http://www.post-gazette.com/pg/06236/716009-96.stm, Aug. 24, 2006.

Sensei, Changing Mindsets with Handsets, http://www.sensei.com, 1 page from website, Copyright 2005, Mar. 13, 2007.

Card Guard: Card Guard receives approval from Israeli Court to become Swiss-based, Press Release, 1 page from website, Oct. 23, 2001, http://www.cardguard.com/newsite/inner.asp?lang=1&news id=43&type=1&cat=44.

* cited by examiner

US 8,560,336 B2

SYSTEM AND METHOD FOR INCREASING COMPLIANCE WITH A HEALTH PLAN

CROSS-REFERENCE TO RELATED APPLICATIONS

This application is a continuation in-part application of U.S. patent application Ser. No. 12/117,190, filed May 8, 2008, titled METHOD FOR TAILORING STRATEGY MESSAGES FROM AN EXPERT SYSTEM TO ENHANCE SUCESS WITH MODIFICATIONS TO HEALTH BEHAVIORS, which is incorporated herein by reference and is a continuation-in-part application of U.S. patent application Ser. No. 11/856,917 filed Sep. 18, 2007 titled SYSTEM AND METHOD FOR REWARDING USERS FOR CHANGES IN HEALTH BEHAVIORS, which is incorporated herein by reference.

TECHNICAL FIELD

The present invention relates generally to systems and methods for assisting with the maintenance of healthy lifestyle habits. More particularly, the present invention is a system and method for track, monitoring, and analyzing data to improve user compliance with personalized diet and exercise plans.

BACKGROUND OF THE INVENTION

The present invention relates generally to systems that promote healthy lifestyles and, more particularly, to weight loss systems. The present invention is an improvement upon existing weight loss systems in that it tracks, monitors, and analyzes data to improve compliance with a personalized health plan. The present invention may be used to motivate dieters as well as keep them on a healthy diet while at the same time allowing flexibility in different dieting aspects including, but not limited to, types of food, amount of food, types of food preparation, and amount of exercise.

Dieting has become an extremely popular activity resulting from people's awareness of the health risks of becoming overweight or obese, a desire to improve one's appearance, and an aspiration to achieve the sense of accomplishment that comes from setting a difficult goal and accomplishing it. However, there is no singular method of dieting that works for every person. Body types, weight loss goals, and preferences vary greatly depending on the individual. Every dieter has individual likes and dislikes as to types of food, times and places to eat, type and length of exercise, eating habits, etc. Due to these differences, many dieters become frustrated with rigid, impersonal diets, and often quit the diet after a short time.

Furthermore, dieters differ on how well they can motivate themselves to continue to adhere to certain dietary guidelines. For example, a dieter who is supposed to only eat a cup of pasta and a vegetable for lunch, but instead decides to eat an ice cream cone as well may be unable to justify such a decision within the diet and decide to give up the diet for the rest of the day. Because such "splurges" are detrimental to the dieter's physical and mental progress, the dieter may find the diet unsustainable.

Many diet plans fail to allow for individualized exercise schedules. Typically, the diet plans suggest the same workout schedule for every person on the diet. For example, the diet plan may incorporate a workout of a half hour, two to three times a week. Such a generalized workout schedule has a number of weaknesses. First, it fails to factor in the type of activity the person is performing. The effectiveness of the exercise depends on what exercise is performed as well as the intensity. A half hour of strolling through a park is simply not as effective as a half hour of running.

Second, it does not allow for individualized ability. For some people, working out for half an hour, two to three times a week, may be physically impossible given their current condition. It may be possible for them in the future, but the person may to a 15 minute workout for until his or her health improves. Other individuals may have the desire and ability to work out for a longer period of time or a greater number of times per week.

Another problem with a general workout schedule is that it fails to factor in the individual's likes and dislikes as to type of activity and time of day to perform the activity. A plan that proposes exercise two to three times a week is easily put aside when the person is busy and distracted by other activities. A person is much more likely to perform an activity that is scheduled or better yet, for which a reminder is provided telling the person to perform a certain activity at a certain time.

Finally, existing diet plans often fail to take into account details regarding the user's dietary information. The two parts of the diet plan—the intake of food and exercise—are generally treated as separate parts of the plan. However, the two are related in that they both have an impact on caloric intake. The more one exercises, the more one can eat. Accounting for both activities allows the impact of one to be applied to the other. For example, a person may eat a large lunch one day and reduce the impact of the lunch by including an extra work out later in the week. Likewise, a person could miss a scheduled workout and compensate for it by eating a smaller meal later in the day.

A highly effective solution to many diet program problems is found through the use of coaching. Research has shown that dieting and weight loss is more successful when the dieter is coached throughout the process. Coaching keeps the dieter motivated, provides positive reinforcement, and introduces a narrowly-tailored plan for each individual participant. However, obtaining a reliable human coach is difficult and prohibitively expensive such that relatively few dieters are actually able to use one.

SUMMARY OF THE INVENTIVE CONCEPT

The present invention addresses the diet plan programs identified above by providing personalized plans to meet the needs and requirements of individual users and determining users' compliance with the plans. It uses tailored messages to "coach" individuals in following their personalized plans. An expert system uses information about an individual's diet and exercise preferences to provide tailored messages related to the plan. The expert system further receives from individuals' responses to messages and other information to determine compliance with personalized plans. Additional tailored messages are designed to increase compliance. As a result, individuals receive personalized instruction in the fields of dieting and exercise without paying the prohibitively expensive fees that are typically associated with personalized instruction. Exemplary embodiments allow the individual to use mobile or portable devices and technology, such as cell phones, PDA's, Blackberrys™, iPhones™, and others, so that the individual has constant access to personalized instruction regarding his or her personalized diet and exercise plan.

The personalized instruction is based on an individual's diet plan preferences, food preferences, meal preparation preferences, and exercise preferences. Behavior challenges are identified and target goals are set. Once the user's plan has been established, typically by providing the preference and other information through an online website, the user is never required to access the site again as the personalized instruction is given through the user's mobile device. The prior art is known to center around "pull" technology, where the user must reach out to the system for the information, and if there is inaction by the user, the instruction will stop. The present invention uses "push" technology, where the instruction is sent to the user, and inaction by the user prompts the system to reach out to the user for corrective actions and encouragement.

It has been found, through the study of behavior informatics, that the use of technology can help people make significant changes in their health. Gradual change, over a longer period of time, is more effective for long-term health solutions, rather than behavior changes that are expected to take place rapidly, over a short period of time. Further, many dieters are more comfortable using familiar technology to assist them with their dieting, as opposed to unfamiliar and possibly uncomfortable office and training room sessions with an actual dietitian and trainer. The present invention incorporates these concepts into a diet and exercise instructional platform based on individuals' preferences to increase the likelihood that individuals will adopt and follow a plan that helps them reach their personal goals.

An expert system determines user compliance with personalized diet and exercise plans and determines appropriate content and display characteristics for messages sent to a user's mobile device such that the user's compliance with the diet and exercise plan is increased. A number of message and display characteristics are monitored for groups of individuals to determine which ones the individuals respond to in a positive manner. Such display characteristics include text messages, pictures, voice patterns, etc. For text messages, the display characteristics may differ from each other in font, size of message, or tone of message.

In one embodiment, the expert system has a number of stored messages and display characteristics from which it may choose. Every time a message relating to the user's diet or physical activity is sent to the user by the expert system, a set of display characteristics is chosen to display the message. The initial set of display characteristics may be randomly chosen or there may be a pre-loaded initial set to be used for every user. The display characteristics are changed periodically and compliance data relating to whether the user was able to adhere to the plan when certain display characteristics are used is stored. This compliance data is stored in a personal profile, unique to each user. Compliance data can be measured in many different ways including, but not limited to, meal plan adherence, acceptance of specific food selections, and adherence to instructions and advice in messages. The expert system then determines which messages and display characteristics achieve the greatest compliance to the dietary and physical activity schedule and goals. These display characteristics are then used when subsequent messages are sent.

In addition to the novel features and advantages mentioned above, other features and advantages will be readily apparent from the following descriptions of the drawings and exemplary embodiments

DETAILED DESCRIPTION

Figure 1:
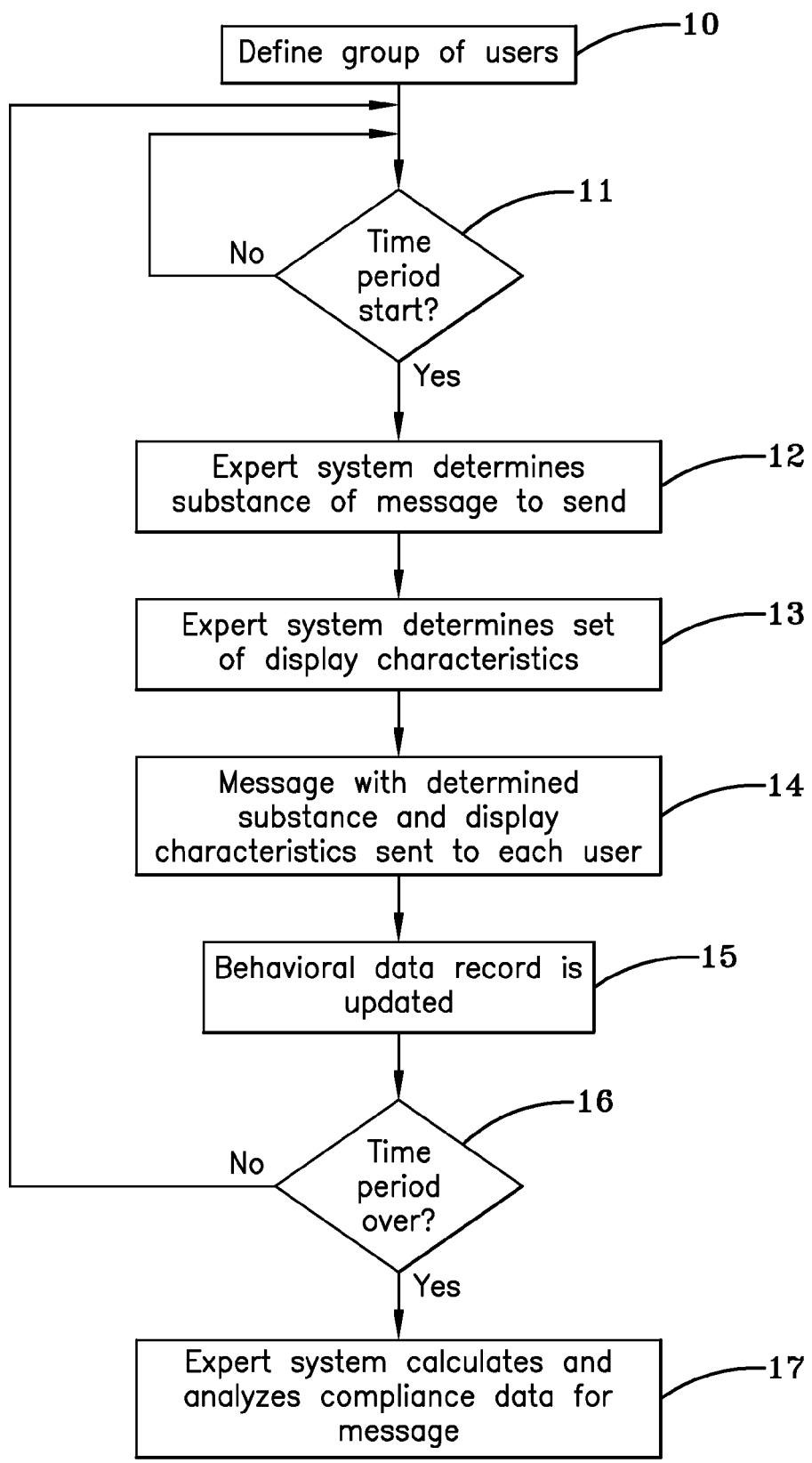
FIG. 1 is a flow chart of a process for determining message effectiveness according to an example embodiment.

Exemplary embodiments provide a predictive modeling system that determines a set of display characteristics to maximize a user's compliance to a personalized diet and exercise program.

Referring to Table 1, data that is tracked and stored for compliance analysis according to an example embodiment is shown. Data may be captured during a user enrollment process and during a user's interactions with the system. Data categories include: customer (data provided by customer related to customer's background or profile, financial, nutrition/diet, behaviors, physical activities, and messages), general (data related to user interactions with website), mobile (data about customers mobile device and its use), marketing (data about customer's introduction to system) and call center (data about customer's interaction with call center). Customer data includes initial profile data as well as diet and exercise plan and behavioral data. Initial profile data is data entered by the user during an enrollment process and may be changed by the user at any time. It may include such information as age, gender, income, height, weight, etc. Nutrition and diet data includes the user's diet plan selection, meal preparation and meal time preferences, preferred foods and substitutions, adherence data, and restaurant and shopping list data. Behavioral data includes identification of problem behaviors and strategies. Physical activity data include preferred activities and current activity level. Message data includes data regarding messages sent and received as well as related timing data.

TABLE 1

| Category | Subcategory | Data Elements | Element Details |
|---|---|---|---|
| Customer | Profile | age | |
| | | gender | |
| | | income | |
| | | height | |
| | | weight | history |
| | | state | |
| | | BMI | history |
| | | education level | |
| | | ethnicity | |
| | | number in household | |
| | | children in household | |
| | | date of enrollment | |
| | | marital status | |
| | | time zone | |
| | | goal weight | |
| | | rate of weight loss selected | history |

TABLE 1-continued

| Category | Subcategory | Data Elements | Element Details |
|---|---|---|---|
| | Financial | household income | |
| | | occupation | |
| | Nutrition/Diet | meal plan | calorie level |
| | | | name |
| | | | change date |
| | | | time on plan |
| | | program | duration |
| | | | start date |
| | | | end date |
| | | | cancel date |
| | | | cancel reason |
| | | meal preparation | |
| | | meal times | breakfast |
| | | | lunch |
| | | | snack |
| | | | dinner |
| | | food eaten most frequently | |
| | | count of suggested menu opt-out | |
| | | substitution | made (in) |
| | | | what was substituted (out) |
| | | | meal |
| | | | meal item |
| | | | meal prep |
| | | foods not selected (don't want) | at enrollment |
| | | | ongoing |
| | | recipes selected | |
| | | adherence (food diary) | breakfast |
| | | | lunch |
| | | | dinner |
| | | | snack |
| | | restaurant | |
| | | shopping list | |
| | Behaviors | problem behaviors | |
| | | strategies | |
| | | strategy success | |
| | | community involvement | member of forum |
| | | | posts |
| | | | response/guidance |
| | Physical Activity | participate | |
| | | current activity level | |
| | | activities | selected |
| | | | schedule |
| | | | level |
| | | | history |
| | | | calories expended |
| | | smoke | |
| | Messages | Messages sent | time |
| | | | time before response |
| | | message type | |
| | | responses | |
| General | website | page views | |
| | | time spent on page | |
| | | repeat views | |
| | | unique visitor | |
| | | returning visitor | |
| | | page before | website |
| | | | search engine |
| | | | city |
| | | number of emails | |
| | | recipe views | download |
| | | article views | downloads |
| | | coupon use | Printed |
| | | | redeemed |
| | | shopping list views | downloads |
| Mobile | | mobile phone number | |
| | | mobile phone model | |
| | | mobile phone manufacturer | |
| | | wireless provider | |
| | | data plan | |
| | | cell phone use | frequency |
| | | | # of times per day |
| | | | times during day |
| | | | average call time |

TABLE 1-continued

| Category | Subcategory | Data Elements | Element Details |
|---|---|---|---|
| | | geo code | lat or UTM (Universal Transverse Mercator Grid) long (or UTM) |
| Marketing | | messaging plan heard about email provider preferred communication IM provider | |
| Call center | | use # calls to RD type of call call status customer data | name mobile number |
| | | length of call resolution | |

As Table 1 indicates, user interactions may be monitored and data may be tracked according to each user's involvement with the system and participation in a diet and exercise program. Information about the frequency and nature of a user's interaction with the system such as the number of messages sent and received by the user over a period of time, the frequency and nature of responses to messages, and the frequency and nature of interaction with a website is collected to later determine user compliance levels.

Table 2 identifies queries that may be performed against the data that is tracked and stored. Queries related to navigation, performance, and operations may be performed. The queries provide an indication of the overall effectiveness of the system and may also be used to determine the effectiveness of individual aspects of the system. For example, various "campaigns" may be developed and promoted to all users or groups of users. User interactions may be monitored and tracked as described previously to determine the effectiveness of the various campaigns.

TABLE 2

| Navigation | Performance | Operations |
|---|---|---|
| Count of active customers compared to goal | Percent increase/decrease in number of active customers per segment (by day/week/month) | Customer acquisition cost per customer segment |
| Count of active customers per account (business) or household (consumer) compared to goal | Number of active customers per account or household | Number of net new prospects (by campaign) |
| Count of products & services used by customers per segment compared to goal | Number of customer referrals by customer segment | Conversion rate of prospects to customers (by campaign) |
| Percent share of wallet, account or household per segment compared to goal | Percent increase/decrease in number of products used by customers per segment (by week/month) | Up-sell/cross-sell success rate by customer segment for additional products and services |
| Percent retention/renewal of active customers by segment compared to goal | Percent increase/decrease in share of wallet, account, or household per segment | Win/loss ratio per account or household per segment |
| Average tenure of customers by segment compared to goal | Customer loyalty ratings per segment | Customer retention cost per segment |
| Number of repeat orders by segment compared to goal | Customer loyalty ratings per distribution channel & interaction touch point | Number of "winback" customers per segment |
| Number of product or service upgrades by segment compared to goal | Increase/decrease in repeat orders/by segment | Percent of customers by segment who have interacted with us (with our partners) within the last quarter |
| Percent of customer outcomes met per segment | Increase/decrease in upgrades per segment | Percent of active customers enrolled in/with activity in customer loyalty program per segment |
| Customer satisfaction ratings per segment | Customer satisfaction ratings per customer scenario & segment | Number of customers "likely to defect" |
| Average time to complete key customer scenarios compared to goals | Task-specific customer satisfaction ratings per interaction touch-point & channel | Product feature- or attribute-specific customer satisfaction ratings |

TABLE 2-continued

| Navigation | Performance | Operations |
|---|---|---|
| Percent of customer responsiveness objectives met compared to goals for critical customer-impacting tasks | Average time to complete key tasks (e.g. Return the correct search result) | Critical cycle times |
| Revenues per customer | Percent accuracy of information | Timeliness (as measured by customer) |
| Profitability per customer by segment | Delivery timeliness and accuracy | Complexity of interactions (# of steps, # of interactions) |
| Average order size by customer segment | Percent cancellations | Inventory availability |
| Average spending per customer by customer segment | End-to-end transaction execution accuracy and speed | Rates of returns, claims, abandonment, |
| Customer lifetime value by customer segment | Growth of customer spending by segment | Defect rates |
| | Customer acquisition and retention costs by segment | Number of customer support requests |
| | Costs-to-serve by segment | Percent customer support interactions with 1-touch resolution |
| | Increase/decrease in sales from new products by segment | Early buying signals by customer segment |
| | Increase/decrease in repeat sales by segment | Costs-to-serve by channels, and touch points |

The present invention may be used to increase compliance by measuring the effectiveness of various messages that are sent to users. Messages may be varied by content and presentation and then sent to different groups of users with similar personal profiles. Within a group, each member may receive identical or similar messages. After a set period of time, compliance data can be calculated for each group. Different messages can then be sent to the same groups or to newly formed groups. Continuing this process creates a comprehensive set of compliance data for a variety of message types and formats. The approach allows numerous data points to be collected for various types and formats of messages and allows an analyst to determine the effectiveness of various messages. More effective messages may be deployed to larger groups of users to increase overall compliance.

In order to build groups of similarly situated individuals, data may be purchased from other parties. Users may be placed into different test groups based upon similarities in their user profiles. Each member of a group may receive at least one message with similar display characteristics. For a period of time, different compliance measures may be recorded for each member in the group. Compliance measures for aggregate groups may be calculated as well. These compliance measures include, but are not limited to, percent increase/decrease in number of active customers, percent increase/decrease in number of products used by customers, and increase/decrease in repeat orders of product or service upgrades. These compliance measures may be based on a large sample size, and allow an analyst to test different display characteristics based on the type of compliance it seeks.

FIG. 1 is a flow chart of a process for determining message effectiveness according to an example embodiment. Once a user group is defined 10, the expert system determines if the time period for measuring message effectiveness has started 11. If the period has started, the expert system determines the substance of the message to be sent 12 to the users. Messages may relate to user goals, meal plans, diet and exercise activity reminders, and requests for responses or input related to an applicable diet and exercise plan. For example, if at least some of the users have accomplished their dietary goals for the week, the expert system may send a positive reinforcement message to the appropriate users. Other users may be asked to provide a current weight or to provide input regarding an activity performed recently. Then, the expert system chooses a set of display characteristics to use with the message based on such information as users' personal profiles 13. The messages are then transmitted for display on the mobile devices using the set of display characteristics 14. The user profiles are updated to indicate what messages were sent and received.

A message characteristics data store for tracking the messages that are sent may also be updated at this time 15. The message characteristics data store may track messages and related display characteristics that are currently in use or have been used for each user, the time period in which they were used, and the resulting changes to each user's personal profile during this time. Once the period for using the specified message characteristics has passed 16, the expert system calculates and analyzes the compliance data for the message 17. The compliance data may be based on the queries identified in Table 2. Messages that result in a greater level of compliance may be used more frequently and adapted for use in other groups or for other purposes.

Figure 2:
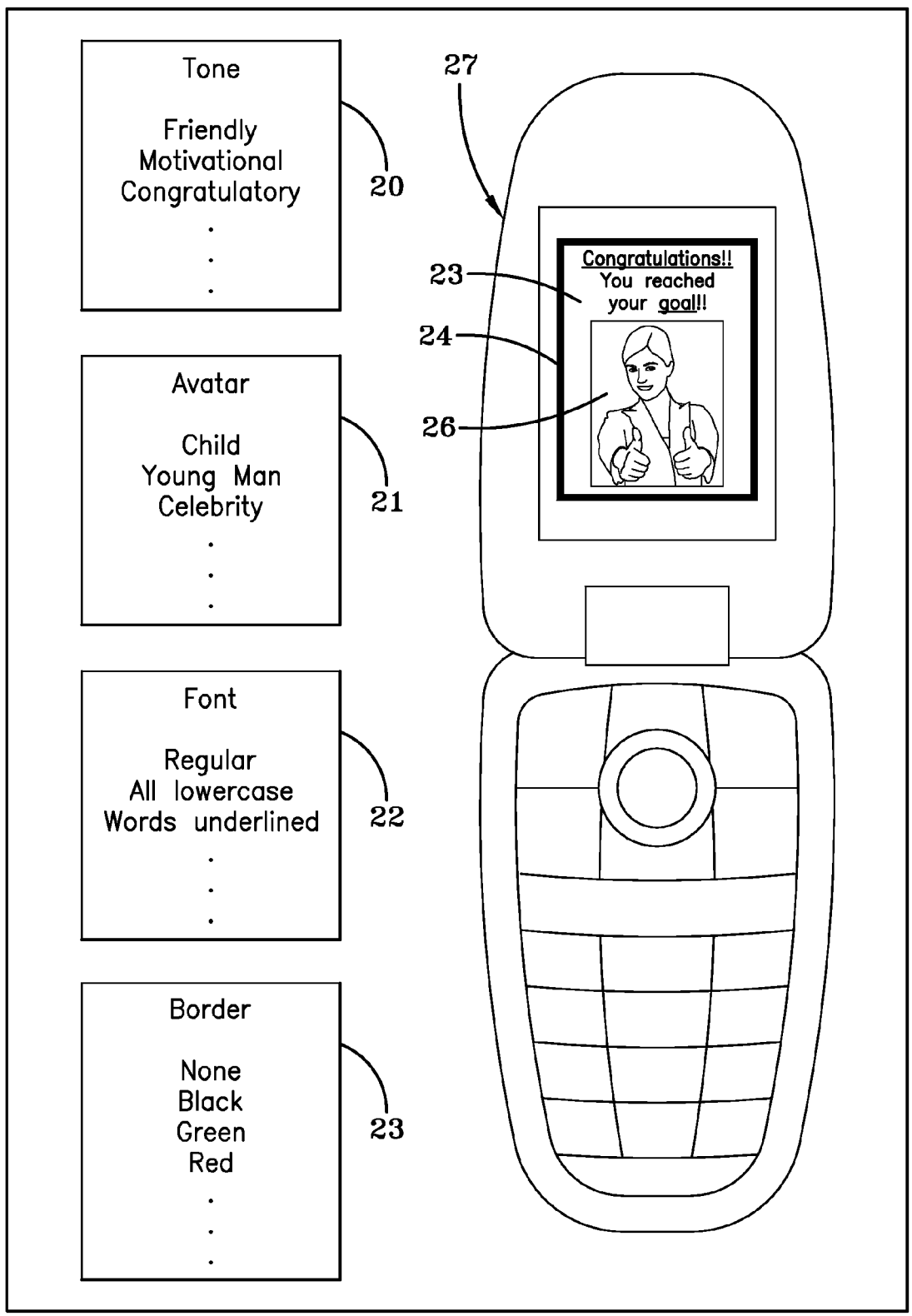
FIG. 2 is an illustration of a process for generating a message by selecting message content and display characteristics according to an example embodiment.

FIG. 2 is an illustration of a process for generating a message by selecting message content and display characteristics according to an example embodiment. In this example, the expert system chooses one of each of the following display characteristics to form a set: message tone (e.g., positive, negative, neutral) 20, an avatar 21, a font 22, and a border 23. The display characteristics are not limited to those shown, but may also include other graphics, certain words, certain sentences, voice tones, etc. The message characteristics are then combined to create a message for display on the mobile device. In this example, a congratulatory message with the positive phrases underlined 24, a black border 25, and a young woman avatar 26 are displayed on a cellular phone 27.

Figure 3:
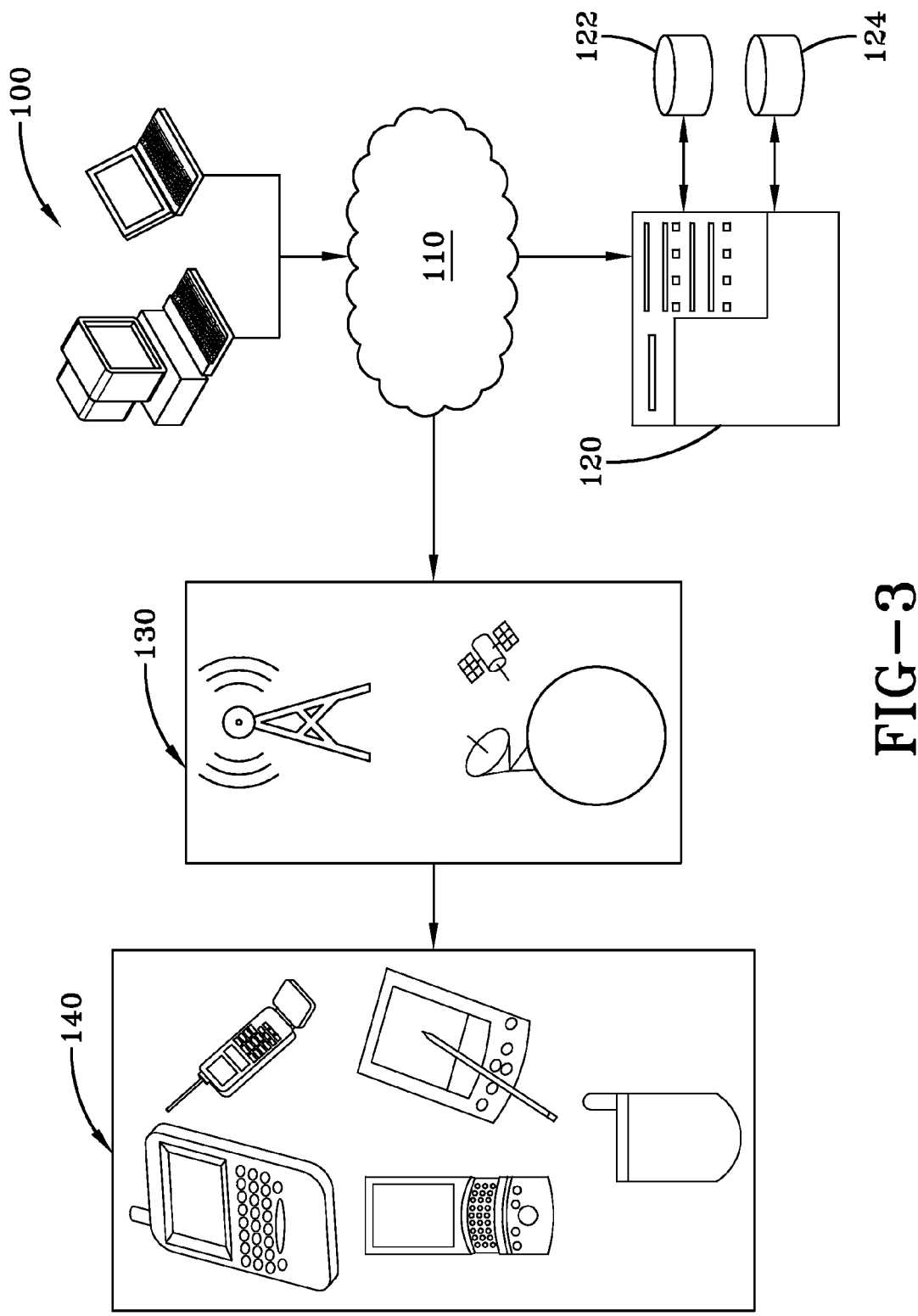
FIG. 3 is an illustration of a physical structure for an example embodiment.

FIG. 3 shows an embodiment of the physical structure of the system. Each of the connections mentioned here permit data to flow in both directions. A laptop or desktop personal computer 100 is connected to the server 120 through the internet 110. The user may connect to a website to create an account and enter personal information and preferences for creating a profile. The server 120 is connected to one or more databases 122, 124 comprising user data, nutrition provider data (nutritional data related to meals offered by a plurality of meal providers), diet, and exercise data, message data, progress data, compliance data, restaurant, shopping, and entertainment establishment data, reward data, and other data as may be required to provide the features and functionality of the present invention. The server 120 is connected to communication networks 130 (comprising various data transmitters and receivers) through the internet 110. The various data transmitters and receivers of the communication networks 130 facilitate communications with the user's portable technology 140 which includes cellular or mobile phones, personal digital assistants, or any other portable device capable of sending and receiving communications through the communication networks 130 and displaying them for a user. An expert system at the server uses the individual's account information, including information about the individual's mobile phone, to tailor and send to the individual messages to reinforce and motivate healthy habits.

In an example embodiment, the expert system is constructed using the J2EE programming language in conjunction with a SQL based database (like Microsoft SQL Server or Oracle DB). AJAX, Active X, and Java components may also be used to handle various aspects of the system. The mobile component of the overall system is constructed using the J2ME programming language sending wireless requests to the expert system over common carrier communication protocols. Communication between the mobile component and the expert system is constructed using XML language structures.

Any embodiment may include any of the optional or preferred features of the other embodiments. The exemplary embodiments herein disclosed are not intended to be exhaustive or to unnecessarily limit the scope of the invention. The exemplary embodiments were chosen and described in order to explain the principles so that others skilled in the art may practice the invention. Having shown and described exemplary embodiments, those skilled in the art will realize that many variations and modifications may be made to affect the described invention. Many of those variations and modifications will provide the same result and fall within the spirit of the claimed invention. It is the intention, therefore, to limit the invention only as indicated by the scope of the claims.

The invention claimed is:

1. A computerized method for tracking, monitoring, and analyzing message data to increase compliance with personalized diet and exercise plans, comprising a server executing programming instructions for:
   a) storing profile data at said server for a plurality of users, said profile data comprising contact information for said users and dietary and exercise preference data for said users;
   b) storing message content at said server comprising a plurality of messages for communicating with said users;
   c) storing display characteristics data at said server comprising display characteristics for formatting said message content;
   d) developing diet and exercise plans at said server for each of said plurality of users, said diet and exercise plans consistent with said dietary and exercise preference data for said plurality of users;
   e) selecting from said message content a plurality of messages for a first group of users selected from said plurality of users, said messages comprising content related to said diet and exercise plans for said first group of users;
   f) selecting from said display characteristics data a first set of display characteristics for formatting said plurality of messages;
   g) setting a first time period for using said first set of display characteristics for formatting said plurality of messages;
   h) transmitting said messages with said set first set of display characteristics to mobile devices for said first group of users using said contact information for said users;
   i) tracking responses at said server to said messages from said first group of users;
   j) selecting from said message content a plurality of messages for a second group of users selected from said plurality of users, said messages comprising content related to said diet and exercise plans for said second group of users;
   k) selecting from said display characteristics data a second set of display characteristics for formatting said plurality of messages;
   l) setting a second time period for using said second set of display characteristics for formatting said plurality of messages;
   m) transmitting said messages with said second set of display characteristics to mobile devices for said second group of users using said contact information for said users;
   n) tracking responses at said server to said messages from said second group of users;
   o) after said first time period, calculating a first set of compliance data for messages with said first set of display characteristics based on responses from said first group of users;
   p) after said second time period, calculating a second set of compliance data for messages with said second set of display characteristics based on responses from said second group of users;
   q) comparing said first set of compliance data and said second set of compliance data to determine which message and associated display characteristics results in a greater level of compliance.

2. The method of claim 1, further comprising the step of updating said profile data for said plurality of users with compliance data for each of said users' compliance with a personalized diet and exercise plan.

3. The method of claim 2, wherein said compliance data for each of said plurality of users is based on a number of messages received and acknowledged over a period of time.

4. The method of claim 1, wherein selecting a first or second set of display characteristics for formatting said messages comprises determining a message tone and selecting a graphic for a message.

5. The method of claim 4, wherein said graphic is an avatar.

6. The method of claim 1, wherein selecting from said message content a plurality of messages comprising content related to said diet and exercise plans comprises selecting messages with content related to a diet and exercise plan goal.

7. The method of claim 1, wherein selecting from said message content a plurality of messages comprising content related to said diet and exercise plans comprises selecting messages with content related to a diet and exercise plan activity reminder.

8. A system for generating messages related to users' diet and exercise plans to send to said users' mobile devices, comprising:
   a database comprising profile data for a plurality of users, said profile data comprising:
      a) contact information for said users;
      b) dietary and exercise preference data for said users; and c) compliance data for said plurality of users wherein said compliance data relates each of said plurality of users' responses to messages regarding diet and exercise plans;

a message content database comprising a plurality of messages for communicating with said users;

a display characteristics database comprising display characteristics for formatting said message content;

an expert system for:

a) developing a diet and exercise plan for each of said plurality of users, said diet and exercise plans consistent with said dietary and exercise preference data for said plurality of users;

b) selecting from said message content a plurality of messages for said plurality of users comprising content related to said diet and exercise plans;

c) selecting from said display characteristics data a plurality of display characteristics for formatting said plurality of messages;

d) setting a time period for using said display characteristics;

e) tracking responses from said plurality of users to said messages formatted with said display characteristics; and f) after said time period, analyzing responses received from said plurality of users during said time period to calculate compliance data for said messages formatted with said display characteristics;

a server for transmitting messages formatted with said display characteristics to and receiving responses from mobile devices for said plurality of users using said contact information.

9. The system of claim 8, wherein said plurality of users have similar profile data as determined by said expert system.

10. The system of claim 8, further comprising a plurality of compliance measures calculated by said expert system from said compliance data.

11. The system of claim 10, wherein said plurality of compliance measures comprises a number of users who have responded to said transmitted messages, a number of users who have not responded to said transmitted messages, and a number of users who have quit a respective diet and exercise plan within a specified period of time.

12. The system of claim 8, wherein said display characteristics comprise a message tone and a graphic.

13. The system of claim 12, wherein said graphic is an avatar.

14. The system of claim 8, wherein said message content comprises a diet and exercise plan goal.

15. The system of claim 8, wherein said message content comprises a diet and exercise plan activity reminder.

\* \* \* \* \*